United States Patent
Mazar et al.

(10) Patent No.: US 7,378,955 B2
(45) Date of Patent: May 27, 2008

(54) SYSTEM AND METHOD FOR CORRELATING BIOMETRIC TRENDS WITH A RELATED TEMPORAL EVENT

(75) Inventors: Scott Thomas Mazar, Inver Grove Heights, MN (US); Bruce H. Kenknight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 74 days.

(21) Appl. No.: 10/335,396

(22) Filed: Jan. 3, 2003

(65) Prior Publication Data

US 2004/0133080 A1    Jul. 8, 2004

(51) Int. Cl.
G08B 1/08 (2006.01)
H04Q 7/00 (2006.01)

(52) U.S. Cl. ............... 340/539.12; 340/523.1; 600/300; 600/301; 607/17

(58) Field of Classification Search ........... 340/539.12, 340/573.1; 600/300, 301, 539; 607/17
See application file for complete search history.

(56) References Cited

U.S. PATENT DOCUMENTS

| | | | |
|---|---|---|---|
| 5,047,930 A | 9/1991 | Martens et al. | |
| 5,306,293 A * | 4/1994 | Zacouto | 607/17 |
| 5,330,505 A * | 7/1994 | Cohen | 607/6 |
| 5,626,630 A | 5/1997 | Markowitz et al. | |
| 5,722,999 A | 3/1998 | Snell | |
| 5,724,985 A | 3/1998 | Snell et al. | |
| 5,732,709 A * | 3/1998 | Tacklind et al. | 600/539 |
| 5,759,199 A | 6/1998 | Snell et al. | |
| 5,822,544 A * | 10/1998 | Chaco et al. | 705/2 |
| 5,860,918 A * | 1/1999 | Schradi et al. | 600/300 |
| 5,904,708 A * | 5/1999 | Goedeke | 607/18 |
| 5,935,081 A | 8/1999 | Kadhiresan | |
| 6,045,513 A | 4/2000 | Stone et al. | |
| 6,093,146 A | 7/2000 | Filangeri | |
| 6,110,522 A * | 8/2000 | Lepper et al. | 427/2.11 |
| 6,190,324 B1 | 2/2001 | Kieval et al. | |
| 6,206,829 B1 * | 3/2001 | Iliff | 600/300 |
| 6,280,409 B1 | 8/2001 | Stone et al. | |
| 6,336,900 B1 | 1/2002 | Alleckson et al. | |
| 6,383,136 B1 | 5/2002 | Jordan | |
| 6,438,407 B1 | 8/2002 | Ousdigian et al. | |
| 6,602,191 B2 * | 8/2003 | Quy | 600/300 |
| 6,665,558 B2 | 12/2003 | Kalgren et al. | |
| 6,735,479 B2 | 5/2004 | Fabian et al. | |
| 6,738,671 B2 | 5/2004 | Christophersom et al. | |

(Continued)

OTHER PUBLICATIONS

"Correlation", [on-line] http://everything2.com/index.pl?node=correlation, (1999 & 2001), 3 pgs.

(Continued)

Primary Examiner—Benjamin C. Lee
Assistant Examiner—Samuel J. Walk
(74) Attorney, Agent, or Firm—Schwegman, Lundberg & Woessner, P.A.

(57) ABSTRACT

Systems and methods for correlating biometric trends with a related temporal event are disclosed. A preferred embodiment utilizes an implantable medical device comprising at least one sensor in electronic communication with a patient management system adapted to temporally analyze and correlate biometric data. Some embodiments of a system disclosed herein also can be configured as an Advanced Patient Management system that helps better monitor, predict and manage chronic diseases.

62 Claims, 3 Drawing Sheets

U.S. PATENT DOCUMENTS

| | | |
|---|---|---|
| 7,043,305 B2 | 5/2006 | KenKnight et al. |
| 7,047,065 B2 | 5/2006 | Kalgren et al. |
| 7,060,031 B2 * | 6/2006 | Webb et al. ............... 600/300 |
| 2001/0007053 A1 | 7/2001 | Bardy |
| 2001/0039503 A1 | 11/2001 | Chan et al. |
| 2001/0047126 A1 | 11/2001 | Quy |
| 2002/0019586 A1 | 2/2002 | Teller et al. |
| 2002/0026103 A1 | 2/2002 | Norris et al. |
| 2002/0026223 A1 | 2/2002 | Riff et al. |
| 2002/0049482 A1 | 4/2002 | Fabian et al. |
| 2002/0107641 A1 * | 8/2002 | Schaeffer et al. ............ 702/19 |
| 2002/0115939 A1 | 8/2002 | Mulligan et al. |
| 2002/0156654 A1 * | 10/2002 | Roe et al. ..................... 705/3 |
| 2003/0144711 A1 | 7/2003 | Pless et al. |
| 2003/0171791 A1 | 9/2003 | KenKnight et al. |
| 2003/0233031 A1 * | 12/2003 | Rice ........................... 600/300 |
| 2004/0073093 A1 | 4/2004 | Hatlestad |
| 2004/0117204 A1 | 6/2004 | Mazar et al. |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2005/0021370 A1 * | 1/2005 | Riff et al. ..................... 705/2 |
| 2006/0195163 A1 | 8/2006 | KenKnight et al. |

OTHER PUBLICATIONS

"Prosecution File History for U.S. Appl. No. 10/093,353", 55 pgs.
"Prosecution File History for U.S. Appl. No. 10/323,590", (as of Oct. 29, 2007),90 pgs.
"Prosecution File History for U.S. Appl. No. 10/323,604", 129 pgs.
"Prosecution File History for U.S. Appl. No. 10/323,606", 139 pgs.
"Prosecution File History for U.S. Appl. No. 10/323,713", (as of Oct. 25, 2007),179 pgs.
"Prosecution File History for U.S. Appl. No. 10/323,859", (as of Oct. 29, 2007),48 pgs.
"Prosecution File History for U.S. Appl. No. 10/323,860", 97 pgs.
"Prosecution File History for U.S. Appl. No. 11/381,051", (as of Oct. 25, 2007),10 pgs.
Anderson, T. W., "R. A. Fisher and multivariate analysis", *Statist. Sci.*, 11(1), (1996),20-34.
Garson, G. D., "Correlation", http://statisticssolutions.com/correlation.htm, Statistics Solutions, Inc.,(Copyright 1998, 2006),12 pgs.
Smith, R.A., et al., "An intranet database for pacemaker patients", *International Journal of Medical Informatics*, 47, (1997),79-82.

* cited by examiner

SYSTEM AND METHOD FOR CORRELATING BIOMETRIC TRENDS WITH A RELATED TEMPORAL EVENT

TECHNICAL FIELD

The present device relates generally to a Patient Management System and particularly, but not by way of limitation, to such a system that is adapted to correlate biometric information or trends to a specific temporal event to provide a snapshot of patient health.

BACKGROUND

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, chronic obstructive pulmonary disease ("COPD"), chronic pain, and epilepsy is event driven, where acute episodes of disease result in hospitalization. In addition to causing considerable physical and emotional trauma to the patient and family, event driven hospitalizations consume a majority of the total health care expenditure allocated to the treatment of heart failure.

An interesting fact about the treatment of acute episodes of disease is that hospitalization and treatment occurs after the acute event has happened. However, most Heart Failure patients exhibit prior non-traumatic symptoms, such as steady weight gain, in the weeks or days prior to the acute episode. If the physician is made aware of these symptoms, it is possible to intervene before the event, at substantially less cost to the patient and the health care system.

Intervention before the event is usually in the form of a re-titration the patient's drug cocktail, reinforcement of the patient's compliance with the prescribed drug regimen, or acute changes to the patient's diet and exercise. Such intervention is usually effective in preventing the acute episode and thus avoiding hospitalization. NYHA Class III and late Class II HF patients often have acute episodes three or four times annually, each episode resulting in hospital stays of three or four days.

However, many acute episodes of disease can be predicted by analyzing biometric trends. Predictive accuracy may be improved by analyzing such biometric trends in view of clinically derived algorithms. In practice, the algorithmic analysis of contemporaneous biometric information or data in reference to a temporal event can report and assist in the identification of a state of patient health or disease progression. Yet, data collection and rapid analysis is a limiting factor in effectively using clinical algorithms to report such states of patient health.

Thus, for these and other reasons, there is a need for a system and method for efficiently and effectively reporting a state of patient health or disease progression by correlating biometric information or trends with a related temporal event and alerting the patient or physician of the state of patient health or disease progression.

SUMMARY

According to one aspect of the invention, there is provided a system and method for correlating sensed biometric information or trends using clinically derived algorithms to report a state of patient health. The report of patient health enables a patient or clinician to examine and further analyze a state of health or disease progression in view of a temporal event that may confer additional clinical meaning to or understanding of the reported state of health. The system also may deliver therapy when configured as an implantable medical device.

In one embodiment, the system comprises at least one sensor to sense biometric data, an interactive database, an analysis module to analyze the biometric data, a correlation module to correlate the biometric data with a temporal event, an electronic transmission module to transmit the output to an interactive communications network, a transformation module to transform transmitted output to a recognizable clinical result, and a display module to display the transformed output. By way of non-limiting example only, a temporal event may comprise a change in patient medication, a heart attack, physical injury, dates of personal interest, or other events.

In another embodiment, the interactive communications network comprises a sensor implanted within a patient, a host in communication with the sensor comprising means to input biometric and/or environmental data to an interactive database, an analysis module to analyze biometric data, and a delivery module that communicates the analyzed data in the form of an identified state of patient health via the communications network.

In yet another embodiment, the system comprises a plurality of interactive databases adapted to store historical and patient population data. In this embodiment, the system is adapted to provide therapy to a patient through a specially adapted implantable medical device based on the identified state of patient health. The implantable medical device may also comprise a sensor. The sensor can be internal or external. External sensors may be adapted to record environmental data. The system also may comprise a diagnostic module for diagnosing the performance of the sensor and the interactive communications network.

In a preferred embodiment of the system and method for correlating biometric trends with a related temporal event, the identified state of patient health is made by analyzing biometric data in view of clinically derived algorithms and monitoring the success of previous identifications of a state of patient health. If warranted by the identified state of patient health, the display module displays a configurable alert for action in the form of a clinically relevant graphic or an audible signal.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The present system and method are described with respect to a system and method that is adapted to report a state of patient health by correlating biometric data or trends with a related temporal event. In this way, the system can provide appropriate therapy to a patient in its embodiment as an implantable medical device or provide a clinician with retrospective environmental and/or perceptual data in time coincidence with objective implanted sensor data. The term "biometric" generally refers to the measurement of a living, human characteristic. The term "Advanced Patient Management" refers to the process of creating and collecting patient specific information, storing and collating the information, and generating actionable recommendations to enable the predictive management of patients with chronic disease. The term "temporal event" refers to events in a patient's environment that may or may not cause a health state change. The term "correlation" refers to time coincident events that have been analyzed for causation and health consequence outcome.

Figure 1:
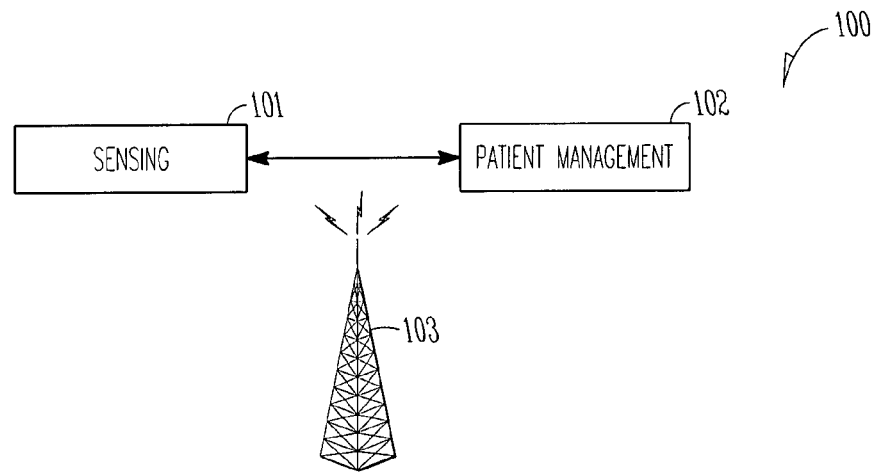
FIG. 1 is a schematic/block diagram illustrating generally, among other things, one embodiment of the system and method for correlating biometric trends with a related temporal event.

FIG. 1 is a schematic/block diagram illustrating generally one embodiment of a system and method for correlating biometric trends with a related temporal event to report a state of patient health. The system 100 further comprises at least one sensor 101 in electronic communication 103 with a patient management system 102 to allow automatic transmission of sensed biometric data to the patient management system 102. Such electronic communication may include wired and/or wireless communication technologies.

Figure 2:
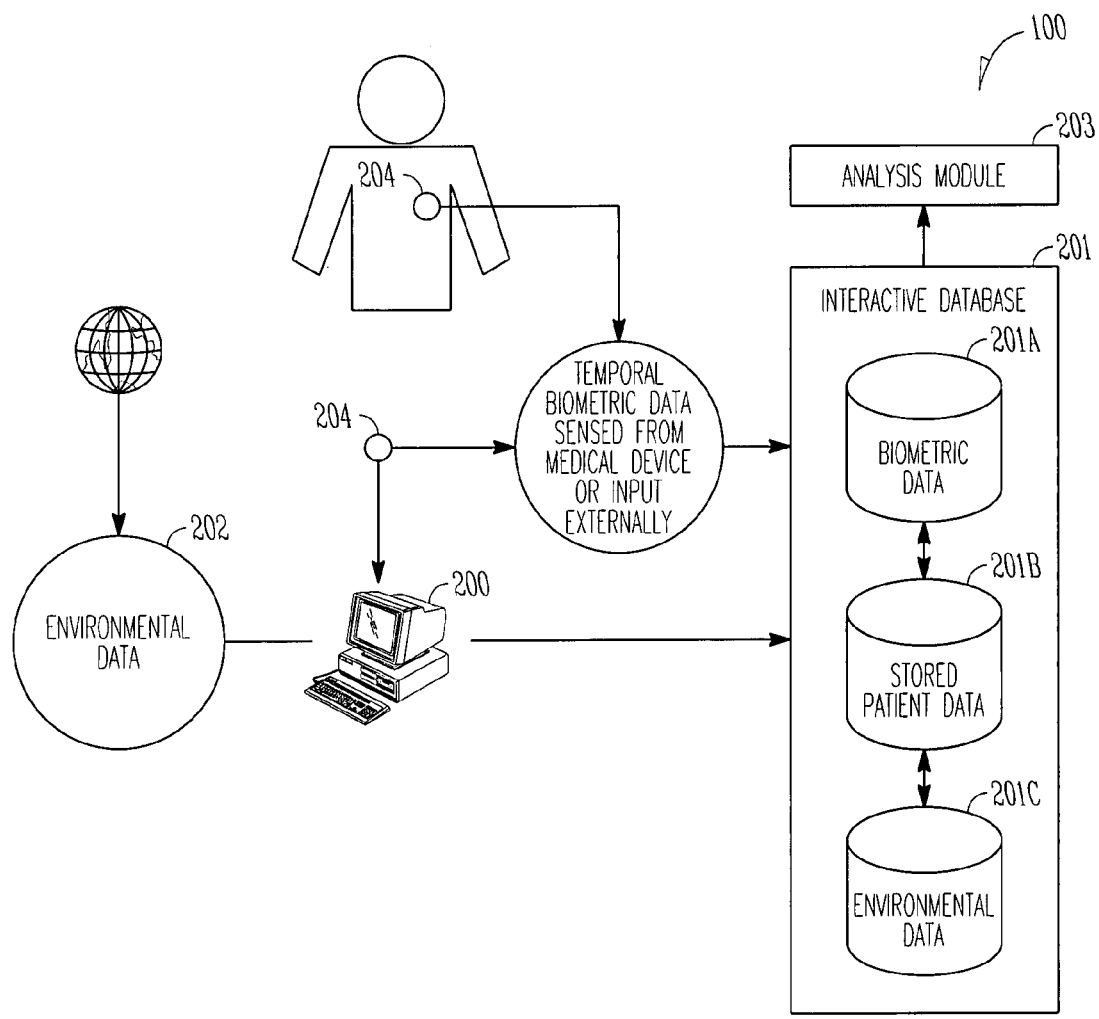
FIG. 2 is a schematic/block diagram illustrating generally, among other things, another embodiment of the system and method for correlating biometric trends with a related temporal event comprising an interactive database and analysis module.

FIG. 2 is a schematic/block diagram illustrating generally another embodiment of the system and method for correlating biometric trends with a related temporal event comprising external means 200 to enter biometric 201a and/or environmental data 202, 201c into at least one interactive database 201 for analysis by an analysis module 203. Environmental data may include temperature, atmospheric pressure, humidity, stress, drug change, diet change, emotional state and/or other objective or subjective data. The database 201 stores data from internal and/or external sensors 204, medical records 201b of a patient, and environmental data 202, 201c. The analysis module 203 identifies a state of patient health based on the information stored in the database 201.

Figure 3:
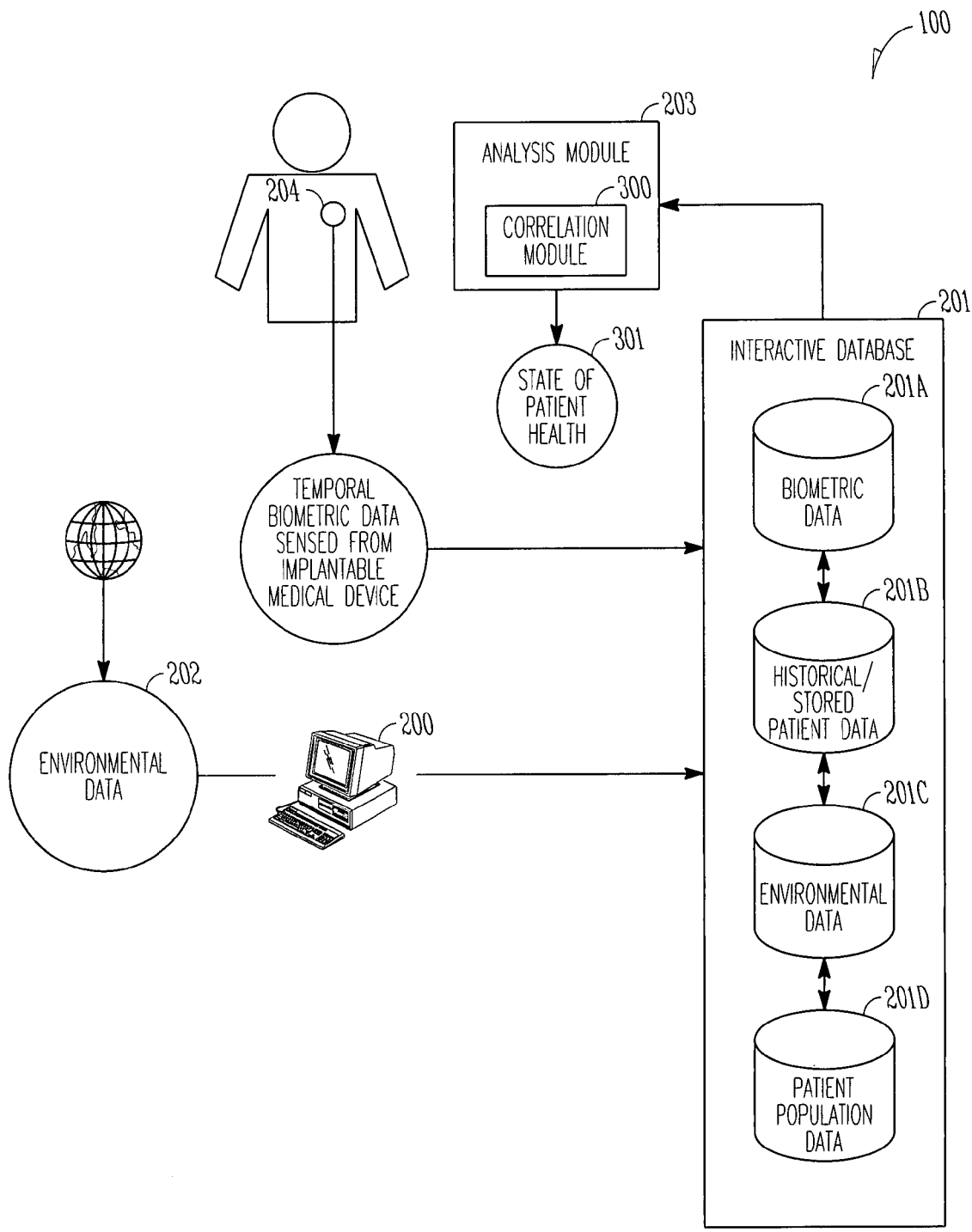
FIG. 3 is a schematic/block diagram illustrating generally, among other things, another embodiment of the system and method for correlating biometric trends with a related temporal event of the present invention comprising a correlation module as a component of an analysis module in electronic communication with an interactive database to report a state of patient health.

FIG. 3 is a schematic/block diagram illustrating generally an embodiment of a correlation module 300 of the system and method for correlating biometric trends with a related temporal event. In addition to at least one internal sensor 204 to sense biometric data and at least one interactive database 201, the system further comprises a correlation module 300 to correlate the biometric data 201a against reference data to create a biometric data set. The reference data may include historical/stored patient data 201b, environmental data 201c and patient population data 201d. Historical patient data may comprise the patient's medical history as manually or electronically entered into the historical/stored patient database 201b. Correlation module 300 may comprise a component of analysis module 203. Biometric 201a and reference data sets 201b, 201c and 201d are transmitted to correlation module 300. Correlation module 300 then correlates the biometric data set with a temporal event to create an output that identifies a state of patient health 301.

Figure 4:
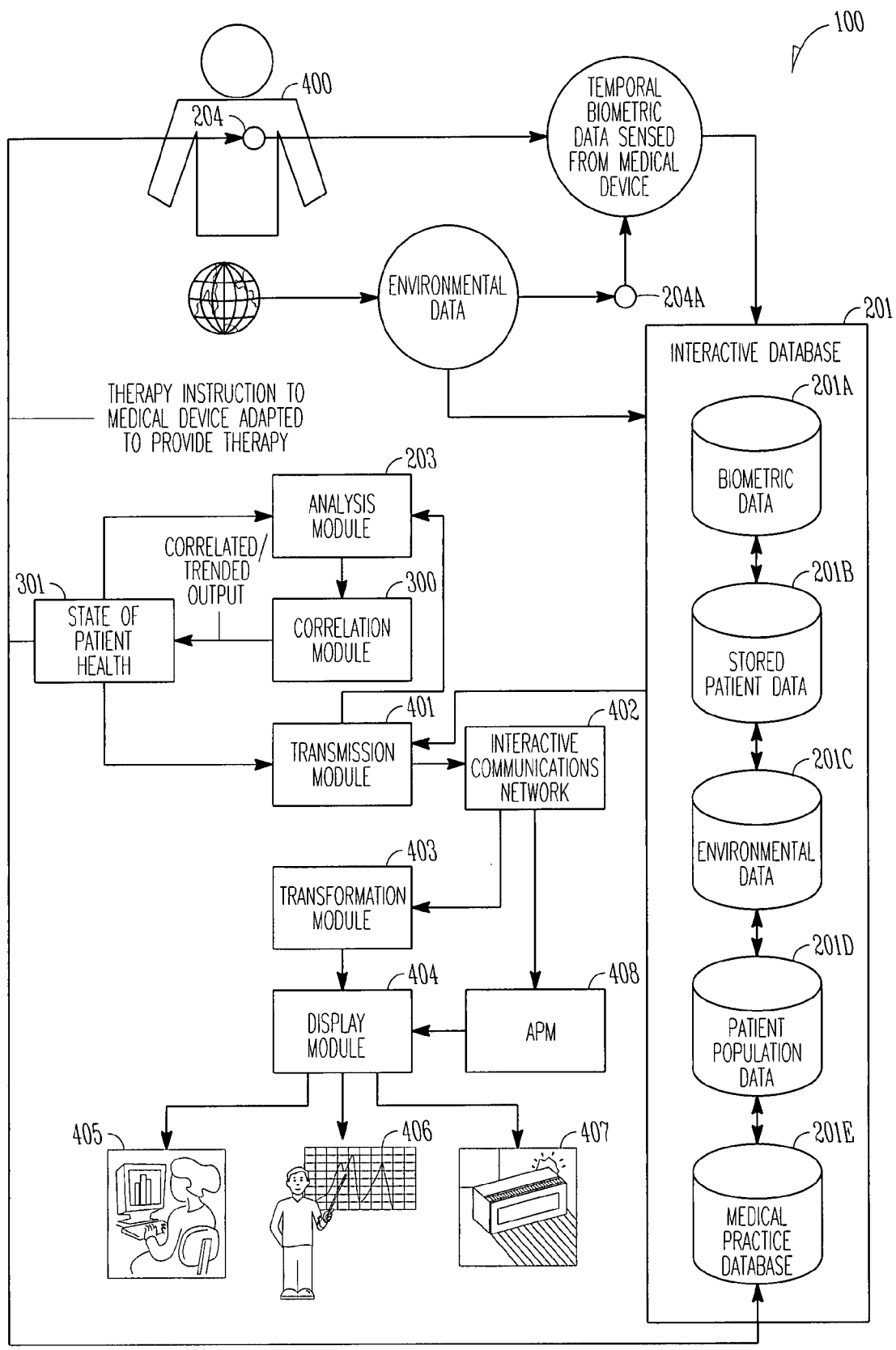
FIG. 4 is a schematic/block diagram illustrating generally, among other things, another embodiment of the system and method for correlating biometric trends with a related temporal event comprising an Advanced Patient Management system in electronic communication with the components of the system.

FIG. 4 is a schematic/block diagram illustrating generally an embodiment of sensors 204 implanted within a patient 400 of the system and method for correlating biometric trends with a related temporal event. The system further comprises an electronic transmission module 401 and an interactive communications network 402. In this embodiment, the correlated output 301 is transmitted via the electronic transmission module 401 to an interactive communications network 402. The output 301 may be transformed by a transformation module 403 and displayed to a clinician or patient 405 via a display module 404 in a human-recognizable format.

In another embodiment as illustrated in FIG. 4, the interactive communications network 402 is in electronic communication with an Advanced Patient Management System ("APM") 408. APM is a system that helps patients, their physicians and their families to better monitor, predict and manage chronic diseases. In the embodiment shown in FIG. 4, the APM system 408 consists of three primary components: 1) an implantable medical device 204 with sensors adapted to monitor temporal biometric data, 2) a Data Management System ("DMS"), which in this embodiment is shown as interactive database 201 and 3) an analytical component 203 adapted to analyze and correlate data from the DMS. APM is designed to support physicians and other clinicians in using a variety of different devices, patient-specific and non-specific data, along with medication therapy, to provide the best possible care to patients. Currently, implanted devices often provide only limited sensing, analysis and therapy to patients. APM moves the device from a reactive mode into a predictive one that allows a clinician to use APM to predict patient health.

In a further embodiment as illustrated in FIG. 4, the interactive database 201 comprises a plurality of interactive databases 201a, 201b, 201c, 201d and 201e. The plurality of interactive databases are adapted to process and store biometric data 201a collected from the sensors, store patient data 201b, environmental data 201c, patient population data 201d and medical practice data 201e. In this embodiment, therapy is provided to a patient via a specially adapted implantable medical device 204 in response to the identified state of patient health 301. A sensor 204a also may be external to a patient 400 to record biometric and environmental data in the database 201.

In a yet another embodiment as illustrated in FIG. 4, the identified state of patient health 301 is based on rules of practicing medicine 201e and revised based on monitoring the success of previous identifications. In this embodiment, the medical practice database 201e comprises clinically derived algorithms of biometric data for automatically reporting a state of patient health 301. The algorithms can be the result of the extraction, codification and use of collected expert knowledge for the analysis or diagnosis of medical conditions. For example, the algorithms can comprise institutional analytical or diagnostic techniques used in specific clinical settings. By reducing the analytical or diagnostic methodologies of institutions like the Cleveland Clinic, the Mayo Clinic or the Kaiser Permanente system to algorithmic expression, a patient will enjoy the benefit of the medical expertise of a leading medical institution without having to visit the institution. The display module 403 is adapted to display a configurable alert for action in the form of a graphical representation 406 of the correlated biometric data and temporal event or an audible signal 407.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including," "includes" and "in which" are used as the plain-English equivalents of the respective terms "comprising," "comprises" and "wherein."

What is claimed is:

1. A method for correlating biometric trends with a related temporal event, comprising the steps of:
   a. automatically sensing biometric data, wherein the biometric data is obtained from an implanted medical device and stored in at least one interactive database;
   b. analyzing the biometric data against a reference data set to create a biometric data set;
   c. correlating the biometric data set with a temporal event to create an output, wherein the temporal event is an environmental event that is capable of causing a health state change in a patient, and wherein the environmental event is selected from a group of events consisting of: a change in temperature, a change in atmospheric pressure, a change in humidity, a change in stress, a change in patient medication, a change in patient diet, and a change in patient emotional state;
   d. electronically transmitting the output to at least one communications device in communication with an interactive communications network;
   e. transforming the output to a human-recognizable format; and
   f. displaying the transformed output, wherein the transformed output comprises the biometric data set displayed with the corresponding temporal event.

2. The method of claim 1, wherein the step of sensing biometric data comprises the further step of sensing the data with at least one sensor.

3. The method of claim 2, wherein the step of sensing biometric data with at least one sensor comprises the further step of sensing the data with a sensor external to a patient.

4. The method of claim 2, wherein the step of sensing biometric data with at least one sensor comprises the further step of sensing the data with a sensor internal to a patient.

5. The method of claim 1, wherein the step of analyzing biometric data comprises the further step of analyzing the data using clinically derived algorithms.

6. The method of claim 1, wherein the step of electronically transmitting the output to at least one communications device comprises the further step of transmitting the output using wireless transmission technologies.

7. The method of claim 1, wherein the step of electronically transmitting the output to at least one communications device comprises the further step of transmitting the output using wired transmission technologies.

8. The method of claim 1, wherein the step of displaying the transformed output comprises the further step of displaying the output to a clinician in a human-recognizable format.

9. The method of claim 1, wherein the step of displaying the transformed output comprises the further step of displaying the output to a patient in a human-recognizable format.

10. The method of claim 1, wherein the step of displaying the transformed output comprises the further step of displaying a configurable alert for action.

11. The method of claim 10, wherein the configurable alert comprises a graphical representation.

12. The method of claim 10, wherein the configurable alert comprises an audible signal.

13. A system for correlating biometric trends with a related temporal event, comprising:
   a. at least one sensor coupled to an implantable medical device to automatically sense biometric data, wherein the biometric data is stored in an interactive database;
   b. an analysis module to analyze the biometric data against a reference data set to create a biometric data set;
   c. a correlation module to correlate the biometric data set with a temporal event to create a correlated output, wherein the temporal event is an environmental event that is capable of causing a health state change in a patient, and wherein the environmental event is selected from a group of events consisting of: a change in temperature, a change in atmospheric pressure, a change in humidity, a change in stress, a change in patient medication, a change in patient diet, and a change in patient emotional state;
   d. an electronic transmission module to transmit the output to at least one communications device in communication with an interactive communications network;
   e. a transformation module to transform the output to a human-recognizable format; and
   f. a display module to display the transformed output, wherein the transformed output comprises the biometric data set displayed with the corresponding temporal event.

14. The system of claim 13, wherein the system comprises an implantable medical device.

15. The system of claim 14, wherein the device is configured to deliver therapy to a patient.

16. The system of claim 13, wherein the network further comprises:
   a. sensors in communication with the interactive communications network, wherein at least one of the sensors is implanted within a patient;
   b. a host, in communication with the sensors via the interactive communications network, the host comprising at least one interactive database and an analysis module, wherein the database temporally stores data from the sensors and medical records of a patient, and the analysis module reports an identification of a state of patient health based on information stored in the database; and
   c. a delivery module that communicates a state of patient health via the communications network for examination.

17. The system of claim 13, wherein the interactive database is a plurality of interactive databases.

18. The system of claim 17, wherein the databases comprise a biometric database, a stored patient data database and an environmental database.

19. The system of claim 17, wherein the databases comprise a biometric database, a historical/stored patient database, an environmental database and a patient population database.

20. The system of claim 17, wherein the databases comprise a biometric database, a historical/stored patient data database, an environmental database, a patient population database and a medical practice database.

21. The system of claim 20, wherein the medical practice database comprises clinically derived algorithms.

22. The system of claim 13, wherein at least one of the sensors is a device external to a patient.

23. The system of claim 13, wherein at least one of the sensors records environmental data that is stored in the database.

24. The system of claim 13, wherein the database stores historical data from a population of patients.

25. The system of claim 13, further comprising a diagnostic module for diagnosing the performance of a sensor and the communications network.

26. The system of claim 13, wherein the communication network uniquely identifies the source of the communication.

27. The system of claim 13, wherein the state of patient health is based on rules of practicing medicine.

28. The system of claim 13, wherein the state of patient health is revised based on monitoring the success of previous predictive diagnoses.

29. The system of claim 13, wherein the analysis module uses clinically derived algorithms to analyze biometric data.

30. The system of claim 13, wherein the display module displays a configurable alert for action.

31. The system of claim 30, wherein the configurable alert for action is a graphical representation of the correlated biometric data and temporal event.

32. The system of claim 30, wherein the configurable alert for action is an audible signal.

33. The system of claim 15, wherein the sensors direct the device to deliver therapy to a patient in response to the state of patient health.

34. A system for correlating biometric trends with a related temporal event, comprising:
   a. at least one sensor coupled to an implantable medical device to automatically sense biometric data, wherein the biometric data is stored in a plurality of interactive databases comprising a biometric database, a historical/stored patient data database, an environmental database, a patient population database, and a medical practice database;
   b. an analysis module to analyze the biometric data against a reference data set to create a biometric data set;
   c. a correlation module to correlate the biometric data set with a temporal event to create a correlated output, wherein the temporal event is an environmental event that is capable of causing a health state change in a patient, and wherein the environmental event is selected from a group of events consisting of: a change in temperature, a change in atmospheric pressure, a change in humidity, a change in stress, a change in patient medication, a change in patient diet, and a change in patient emotional state;
   d. an electronic transmission module to transmit the output to at least one communications device in communication with an interactive communications network;
   e. a transformation module to transform the output to a human-recognizable format; and
   f. a display module to display the transformed output, wherein the transformed output comprises the biometric data set displayed with the corresponding temporal event.

35. The system of claim 34, wherein the system comprises an implantable medical device.

36. The system of claim 35, wherein the device is configured to deliver therapy to a patient.

37. The system of claim 34, wherein the network further comprises:
   a. sensors in communication with the interactive communications network, wherein at least one of the sensors is implanted within a patient;
   b. a host, in communication with the sensors via the interactive communications network, the host comprising at least one interactive database and an analysis module, wherein the database temporally stores data from the sensors and medical records of a patient, and the analysis module reports an identification of a state of patient health based on information stored in the database; and
   c. a delivery module that communicates a state of patient health via the communications network for examination.

38. The system of claim 34, wherein at least one of the sensors is a device external to a patient.

39. The system of claim 34, wherein at least one of the sensors records environmental data that is stored in the database.

40. The system of claim 34, wherein the database stores historical data from a population of patients.

41. The system of claim 34, further comprising a diagnostic module for diagnosing the performance of a sensor and the communications network.

42. The system of claim 34, wherein the communication network uniquely identifies the source of the communication.

43. The system of claim 34, wherein the state of patient health is revised based on monitoring the success of previous predictive diagnoses.

44. The system of claim 34, wherein the display module displays a configurable alert for action.

45. The system of claim 44, wherein the configurable alert for action is a graphical representation of the correlated biometric data and temporal event.

46. The system of claim 44, wherein the configurable alert for action is an audible signal.

47. The system of claim 36, wherein the sensors direct the device to deliver therapy to a patient in response to the state of patient health.

48. A method comprising:
sensing biometric data using an implanted medical device;
electronically transmitting the biometric data to a database;
determining a correlation between the biometric data and a temporal event, wherein the temporal event is selected from a group of events consisting of: a change in temperature, a change in atmospheric pressure, a change in humidity, a change in stress, a change in patient medication, a change in patient diet, and a change in patient emotional state; and
displaying the biometric data and the correlated temporal event in a formatted output.

49. The method of claim 1, wherein the environmental event comprises a change in temperature.

50. The method of claim 1, wherein the environmental event comprises a change in atmospheric pressure.

51. The method of claim 1, wherein the environmental event comprises a change in humidity.

52. The method of claim 1, wherein the environmental event comprises a change in stress.

53. The method of claim 1, wherein the environmental event comprises a change in patient medication.

54. The method of claim 1, wherein the environmental event comprises a change in patient diet.

55. The method of claim 1, wherein the environmental event comprises a change in patient emotional state.

56. The system of claim 13, wherein the environmental event comprises a change in temperature.

57. The system of claim 13, wherein the environmental event comprises a change in atmospheric pressure.

58. The system of claim 13, wherein the environmental event comprises a change in humidity.

59. The system of claim 13, wherein the environmental event comprises a change in stress.

60. The system of claim 13, wherein the environmental event comprises a change in patient medication.

61. The system of claim 13, wherein the environmental event comprises a change in patient diet.

62. The system of claim 13, wherein the environmental event comprises a change in patient emotional state.

* * * * *

UNITED STATES PATENT AND TRADEMARK OFFICE
CERTIFICATE OF CORRECTION

PATENT NO. : 7,378,955 B2 Page 1 of 1
APPLICATION NO. : 10/335396
DATED : May 27, 2008
INVENTOR(S) : Mazar et al.

It is certified that error appears in the above-identified patent and that said Letters Patent is hereby corrected as shown below:

Title Pg, Item (56), in column 2 (below U.S. Patent Documents), line 1, below "6738671 B2  5/2004  Christophersom et al."
insert -- FOREIGN PATENT DOCUMENTS
    WO    WO-01/03575 A1    1/2001 --.

In column 7, line 20, in Claim 18, after "patient" delete "data".

In column 7, line 27, in Claim 20, after "patient" delete "data".

In column 8, line 1, in Claim 34, after "patient" delete "data".

Signed and Sealed this

Twenty-sixth Day of August, 2008

JON W. DUDAS
*Director of the United States Patent and Trademark Office*